United States Patent
Oyama et al.

(10) Patent No.: US 6,544,478 B1
(45) Date of Patent: Apr. 8, 2003

(54) QCM SENSOR

(75) Inventors: Noboru Oyama, 3-10-7, Kichijojihigashi-cho, Musashino-shi, Tokyo 180-0002 (JP); Tetsu Tatsuma, Tokyo (JP); Yoshihito Watanabe, Tokyo (JP); Osamu Hatozaki, Tokyo (JP); Kaoru Kitakizaki, Saitama (JP); Masanori Haba, Chiba (JP); Takayuki Noguchi, Tokyo (JP)

(73) Assignees: Kabushiki Kaisha Meidensha, Tokyo (JP); Noboru Oyama, Tokyo (JP)

( * ) Notice: Subject to any disclaimer, the term of this patent is extended or adjusted under 35 U.S.C. 154(b) by 0 days.

(21) Appl. No.: 09/341,465

(22) PCT Filed: Nov. 2, 1998

(86) PCT No.: PCT/JP98/04948
§ 371 (c)(1), (2), (4) Date: Jul. 12, 1999

(87) PCT Pub. No.: WO00/26636
PCT Pub. Date: May 11, 2000

(51) Int. Cl.$^7$ .............. G01N 27/00
(52) U.S. Cl. .............. 422/82.01; 422/68.1; 422/88; 422/98; 436/151
(58) Field of Search .............. 422/88, 68.1, 69, 422/98, 82.01; 436/149, 151

(56) References Cited

U.S. PATENT DOCUMENTS 5,201,215 A    4/1993  Granstaff et al. .......... 73/54.41
5,684,276 A  * 11/1997  Altemir ................. 177/210
5,706,840 A    1/1998  Schneider et al. ......... 134/56 R
6,033,852 A  *  3/2000  Andle et al. .............. 310/311

OTHER PUBLICATIONS

Lin, Z., et al., "Operation of an Ultrasensitive 30–MHz Quartz Crystal Microbalance in Liquids," Anal. Chem., vol. 65, No. 11, pp. 1546–1551 (1993).

Satoh, H., et al., "Surface Acoustics Wave Propagation Characteristics on a Langasite Crystal Plate," Japanese Journ. Appl. Phys., vol. 36, No. 5B, pp. 3071–3073 (1997).

* cited by examiner

Primary Examiner—Lyle A. Alexander
(74) Attorney, Agent, or Firm—Foley & Lardner

(57) ABSTRACT

A QCM sensor including a sensor device, the sensor device having a crystal substrate, on both of front and rear surfaces of which a pair of electrodes are disposed so as to oppose with each other and the QCM sensor detecting and quantitatively analyzing components of a sample from either a variation in a fundamental resonant frequency or a variation in an impedance when a surface of one of the pair of electrodes is immersed into either a sample gas or a sample solution. The sensor device is arranged in a multi-channel structure such that four mutually opposing electrodes (11A through 14A, 12B through 14B) are disposed on both front and rear surfaces of the crystal substrate 10, each electrode being arranged to enable a fixation of a receptor which is different for each component of a sample to be detected and quantitatively analyzed, whereby the QCM sensor detects and quantitatively analyzes once the components of one sample different for different electrodes.

16 Claims, 9 Drawing Sheets

| RESONANT FREQUENCY f0 (MHz) | DISTANCE TO ADJACENT ELECTRODE (mm) |
|---|---|
| 5 | 6.7 |
| 10 | 3.3 |
| 20 | 1.7 |
| 30 | 1.1 |
| 50 | 0.67 |
| 100 | 0.33 |
| 150 | 0.22 |

| | Fs (MHz) | -ΔFs (Hz) | R1 (Ω) | ΔR1 (Ω) |
|---|---|---|---|---|
| IN THE AIR (CRITERION) | 10.093134 | — | 27.749 | — |
| WHEN WATER IS ADDED ON ONLY CH1 | 10.086776 | 6358 | 33.230 | 5.481 |
| WHEN WATER IS ADDED ON ONLY CH2 | 10.093106 | 28 | 27.744 | -0.005 |
| WHEN WATER IS ADDED ON ONLY CH3 | 10.093134 | 0 | 27.758 | 0.009 |
| WHEN WATER IS ADDED ON ONLY CH4 | 10.093107 | 27 | 27.674 | -0.075 |

$$f_0 = v/2t_q \quad \cdots (1)$$

$$v = (\mu_q / \rho_q)^{1/2} \quad \cdots (2)$$

FIG.13

$$\Delta f = -\frac{2f_0^2 \Delta m}{A_{PIEZO}(\mu_q \rho_q)^{1/2}} = \frac{-C_f \Delta m}{A_{PIEZO}} \quad \cdots (3)$$

FIG.14

$$\Delta f = -f_0^{3/2} \sqrt{\frac{\eta_L \rho_L}{\pi \mu_q \rho_q}} = -C_f \sqrt{\frac{\eta_L \rho_L}{2\omega_0}} \quad \cdots (4)$$

FIG.15

$$C_f = \frac{2f_0^2}{\sqrt{\mu_q \rho_q}} \quad \cdots (5)$$

QCM SENSOR

TECHNICAL FIELD

The present invention relates to a QCM (Quartz Crystal Microbalance) sensor for detecting and estimating (quantitatively analyzing) components of a sample from either a variation in an oscillation frequency of a quartz oscillator or a variation in an impedance when a surface of an electrode of the quartz oscillator is immersed into a sample gas or a sample solution, and particularly relates to a multi-channel QCM sensor device suitable for detecting and estimating simultaneously a plurality of components from the same sample.

BACKGROUND OF THE INVENTION

In chemical and bio-chemical fields, it is important to quantitatively analyze a reaction quantity and a mass of a product. However, it has been difficult to obtain a sufficient detection sensitivity to an extremely minute quantity of reaction.

In chemical and bio-chemical sensors to which a microbalance principle is applied using a crystal oscillator of AT-cut have been developed and have been noticed to the public.

The crystal oscillator of AT-cut has its main resonant frequency inversely proportional to a thickness of a disk of the oscillator. In this case, when the components of the sample are film formed on surfaces of electrodes of the crystal oscillator or an adsorption of a substance occurs on the surface of the electrodes, a frequency shift phenomenon occurs which corresponds to a weight of the substance present on the surface per unit flat surface area.

The QCM sensor is an application of the above-described frequency shift phenomenon. Since the crystal oscillator of AT-cut has a frequency characteristic which is stable in a wide range of temperature, a stable detection sensitivity can be expected. If a condition is established, it is possible for the QCM sensor to detect an adsorption substance of 1 through 10 ng on a real time basis.

A relationship between the substance quantity of the adsorption and the shift quantity of the frequency will be described below.

Figure 12:
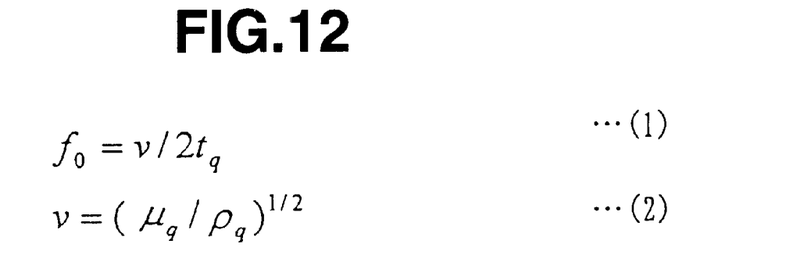
FIG. 12 is equations (1) and (2) on a resonant frequency of a crystal oscillator of AT-cut.

First, the oscillation frequency of the crystal oscillator of AT-cut is expressed in an equation (1) and an equation (2) shown in FIG. 12.

In each equation (1) and (2), fo: a main resonant frequency of the crystal oscillator, v: a sound velocity in the crystal, tq: a thickness of the crystal, $\mu q$: a shear elasticity constant, and $\rho q$: a density of the crystal.

Figure 13:
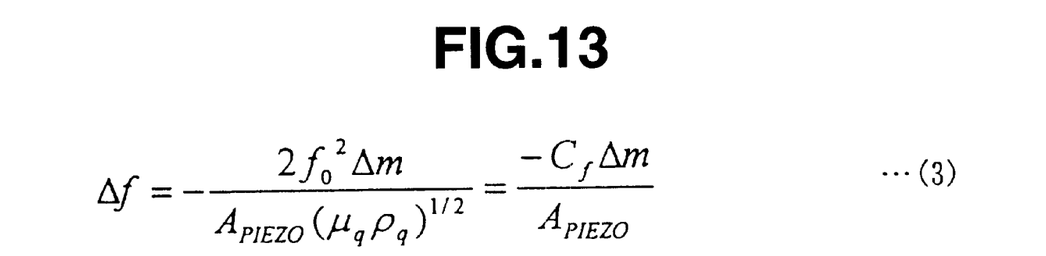
FIG. 13 is a numerical equation (3) representing a frequency variation by means of the crystal.

A mass change $\Delta m$ generated on the surface of the crystal oscillator having the main resonant frequency fo is expressed in an equation (3) of FIG. 13 by evolving the relation equation between the main resonant frequency and thickness of the crystal.

In the equation (3), $\Delta f$ denotes a frequency variation due to an addition of a mass, Apiezo denotes an electrical effective area, Cf denotes a whole sensitivity.

Figure 14:
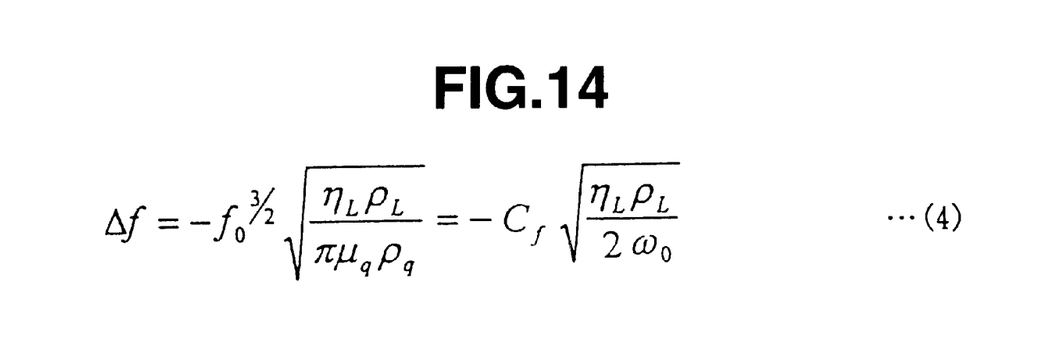
FIG. 14 is a numerical equation representing a frequency variation in a case where the crystal oscillator is used in a liquid.

If the crystal oscillator having the main resonant frequency fo of the equation (3) be rewritten as in the equation (4) shown in FIG. 14 since $\Delta f$ is affected by the viscosity of the liquid and density thereof.

It is noted that $\eta_L$ denotes a viscosity of the solution, $\rho_L$ denotes a density of the solution, and $\omega_0 = 2\pi f_0$.

Figure 15:
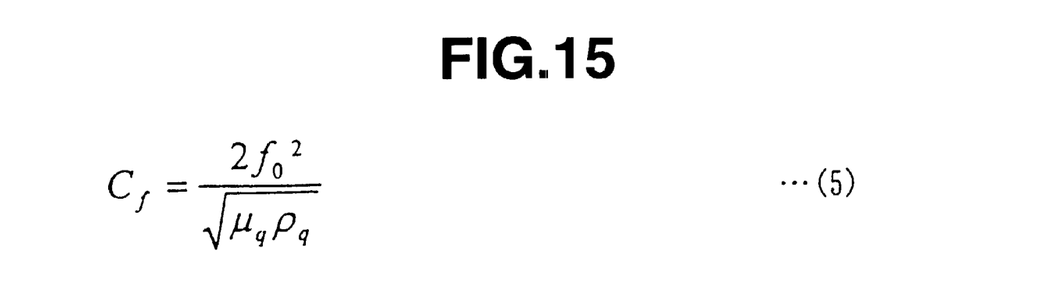
FIG. 15 is a numerical equation representing a whole sensitivity.

In addition, the whole sensitivity Cf is expressed in the equation (5) of FIG. 15.

As appreciated from the above equation of (5), it is important to increase the main resonant frequency fo to increase the whole sensitivity Cf. Since the whole sensitivity Cf itself is a function of the frequency, a deviation $\Delta f$ of the frequency is actually dependent upon a 3/2 power of the main resonant frequency fo.

Figure 16:
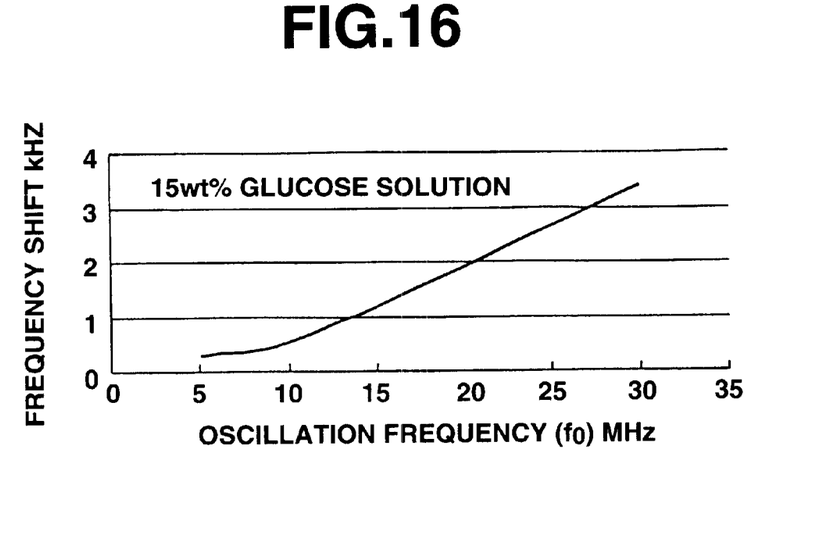
FIG. 16 is a characteristic graph representing a frequency dependent characteristic of the sensitivity on the sensor device.

Hence, as the main resonant frequency of the crystal oscillator used as the sensor is increased, a high sensitivity sensor can be used. For example, FIG. 16 shows a characteristic graph plotting the frequency shift quantity $\Delta f$ of the crystal oscillator immersed into a glucose solution of 15 wt % (weight percents). As the main resonant frequency fo becomes increased, it will be appreciated that the deviation of the resonant frequency with respect to the adsorption quantity on the same electrode surface.

As described above, the crystal oscillator of AT-cut uses a thickness-slip mode, the main resonant frequency fo is inversely proportional to its thickness tq. In addition, it is necessary for the crystal oscillator to reduce its electrode effective area in proportion to the frequency in order to obtain a sufficient value of $\gamma$ ($\gamma$ denotes a ratio between a parallel capacitance and a serial capacitance in an equivalent circuit of the crystal oscillator and usually approximately 250 in the case of the crystal oscillator of AT-cut).

For the reason described above, it becomes necessary to provide the crystal oscillator having a small electrode area and a thin crystal thickness for that used for a high-frequency application purpose.

Figure 17:
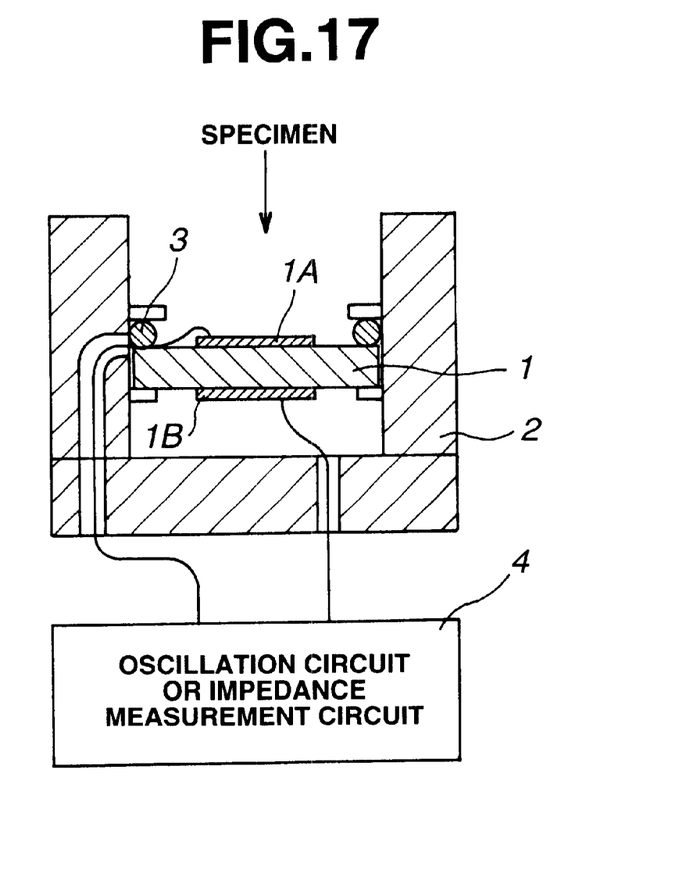
FIG. 17 is a conventional example of a QCM sensor device.

On the other hand, in order to realize the QCM sensor, there is an arrangement of the QCM sensor in which the crystal oscillator 1 is held within a vessel 2, only the oscillator surface is exposed to be immersed into the sample, its surrounding of the surface is sealed by means of O ring or so on, and electrodes 1A and 1B of the crystal oscillator 1 are connected across an oscillation circuit or an impedance measurement circuit 4 via lead wires, as shown in FIG. 17.

Since the QCM sensor arranged as described above has a crystal substrate which is thin in accordance with the high frequency purpose crystal oscillator, the substrate often becomes distorted (have a strain) or cracked due to a stress imposed on its sealing portion.

Hence, it is difficult to put the sensor device for the high frequency application into practice. However, a method of making the QCM sensor device through a method of making only a center portion of the substrate at a single cell thinner by means of an etching process has been proposed by Zuxuan Lin et al.

In this case, a portion of the crystal oscillator corresponding to a frame of the crystal oscillator has a thickness corresponding to 5 through 6 MHz (corresponding to 0.3 mm) conventionally used and a large distortion of that portion due to the sealing does not occur. In addition, since the portion which has been thinned has the sufficiently small-sized electrode area to provide an energy trap, an effect of the frame is difficult to receive.

Although the QCM sensor to increase its sensitivity can be achieved by the above-described method, any of the conventional QCM sensors is arranged in such a manner that only one sensor is within a single cell. Hence, any conventional QCM sensor can only measure one a single component from one sample.

This makes the measurement of the respective components of the sample restricted to one-cell-for-one-sample with the cells capable of detecting and measuring the respective cells in order to detect and estimate the respective components from the sample solution including the plurality of components. Consequently, it takes a long time to measure the individual components and a measurement cost becomes increased.

In order to shorten the measurement time, a multi-channel type QCM sensor has been proposed. Such a multi-channel type QCM sensor as described above is arranged as follows: a plurality of crystal oscillators are attached onto a substrate holder, a probe is moved on each crystal oscillator, and a data on each component of the sample is obtained for each crystal oscillator.

However, in the multi-channel type QCM sensor described above, the application of an electrical field is caused by the movement of the probe.

A deviation of the relative position of the probe to each crystal oscillator causes the oscillation frequency and the impedance to be varied.

The conventional multi-channel QCM sensor is difficult to be actually arranged to maintain accurately a measurement condition such as the resonant frequencies of the crystal oscillators.

In addition, a consequent stable measurement cannot be desirably be achieved by the conventional QCM sensor.

It is therefore an object of the present invention to provide a QCM sensor which enables a stable measurement of each component of a sample with a sensor portion being in a multi-channel structure and enables a highly accurate measurement thereof with a fundamental resonant frequency of a sensor portion increased to a high frequency point.

DISCLOSURE OF THE INVENTION

In addition, the sensor device according to the present invention has a structure such that a rate L/t between a thickness t of the crystal substrate and a distance L between the adjacent electrodes is equal to or above 20 if the electrodes of the multi-channel structures are circular.

According to the structure described above, a highly accurate measurement without mutual interference between the adjacent electrodes can be made in order to once detect and estimate the components different for the electrodes by one sample and a whole dimension of the sensor device can be minimized.

The sensor device according to the present invention is a multi-channel structure in which the electrodes are adjoined and disposed at a plurality of portions, a receptor different for each component of the sample to be detected and to be estimated being fixed onto each electrode. This structure can detect and estimate once the components different for each electrode by one sample. In addition, since it becomes unnecessary to operate the probe to be moved on the conventional multi-channel type QCM sensor, the stable measurement can be made without variation in the measurement condition.

Furthermore, the structure becomes simple since the device structure is only the sensor device and the measurement device.

The crystal substrate of the sensor device according to the present invention is provided with a separation groove to reduce an oscillation energy between the adjacent electrodes. This structure causes a leakage of the oscillation energy between the electrodes to be attenuated into the separation groove and permits a stable measurement frequency with the distance between the electrodes shortened.

The crystal substrate of the sensor device according to the present invention has the structure such that a thickness of an electrode forming portion becomes thinner than that of the surrounding portion.

The crystal substrate of the sensor device according to the present invention can enhance a mechanical strength of the substrate to secure its holding and can use it in the high frequency range with the thickness of the electrode portion thinned.

The sensor device according to the present invention includes a sensor main body in which the electrode forming portion using a high-frequency thin crystal substrate is made thinner than the thickness of the surrounding portion and a substrate holder made of a crystal substrate or a quartz substrate, and whose thickness is larger than the sensor device main body, and onto which the sensor device main body is adhered.

According to this structure, a quantity of etching to make the electrode portion thinner in order to make a high frequency sensor device is reduced so that the crystal substrate can be protected from a crack.

It is noted that in the sensor device according to the present invention, a Langasite crystal having a large mechanical coupling coefficient may be used in place of the crystal substrate.

BEST MODE FOR CARRYING OUT THE INVENTION (First Embodiment)

Figure 1A:
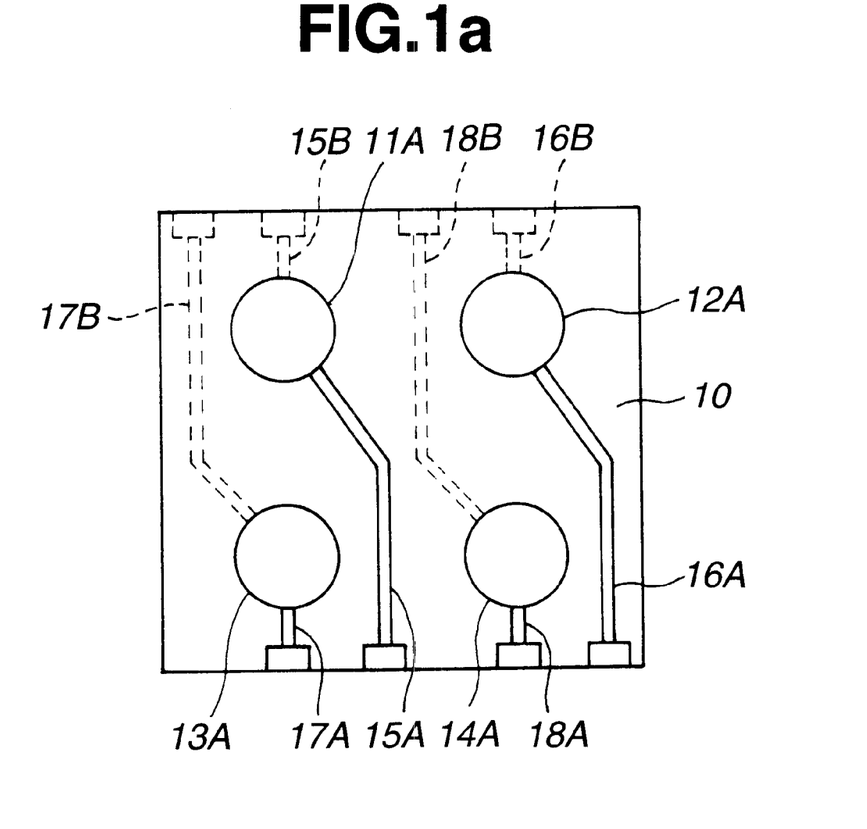
FIGS. 1a and 1b are elevational view and side view of a sensor device in a first preferred embodiment according to the present invention, respectively.
Figure 1B:
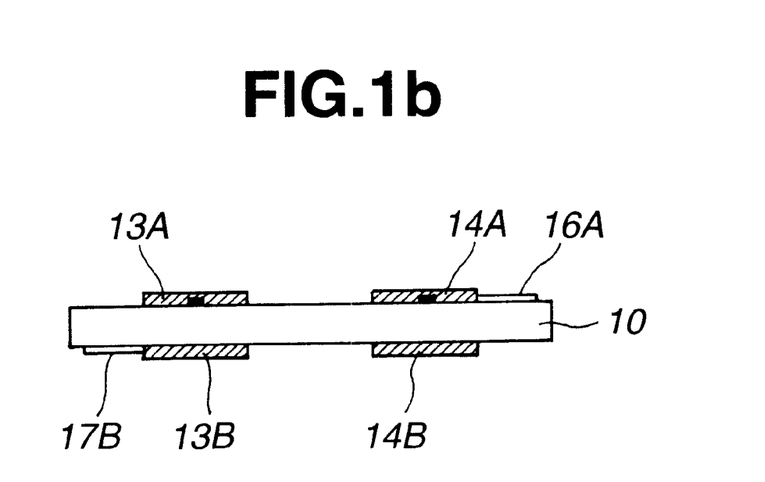

FIGS. 1a and 1b show a plan view and a side view of a structure of a multi-channel QCM sensor device in a first preferred embodiment according to the present invention.

A crystal substrate 10 is constituted by a crystal of AT-cut having a quadrilateral shape and an uniform thickness. Circular electrodes 11A, 12A, 13A, 14A and 11B, 12B, 13B, 14B (each made of a gold or platinum) are mutually formed on front and rear surfaces of the crystal substrate 10 by means of a sputtering method. Each electrode 11A through 14A and 11B through 14B is drawn out to a corresponding terminal surrounding the crystal substrate via lead wires 15A through 18A and 15B through 18B.

It is noted that the thickness of the crystal substrate 10 is determined according to a fundamental (or main) resonant frequency fo (5 MHz or 10 MHz) in accordance with the equations (1) and (2). In addition, the area of each electrode is determined as a factor determining the sensitivity in the equations (3) through (5).

In order to arrange the QCM sensor using the sensor device thus structured, in the same manner as shown in FIG. 17, one of the front or rear surface is immersed into a sample. Receptors which are mutually different according to the components to be tried to be detected and estimated (quantitatively analyzed) from the sample are formed on one of the front or rear surface of the electrodes 11A through 14A which is immersed into the sample.

For example, an "anti-measles virus antibody" to detect and estimate a virus of "measles" is fixated onto the electrode 11A and a grippe antigen to detect and estimate the antibody of a grippe is fixated onto the opposing electrode 11B.

In addition, terminals drawn out of the respective electrodes 11A through 14A and 11B through 14B are connected to individual oscillation circuits or impedance measurement circuits or switchingly connected to a single oscillation circuit in a time division mode.

Therefore, variations in the oscillation frequencies or in impedances when the electrodes 11A through 14A are immersed into the sample are individually measured.

In the sensor device arranged as described above and the QCM sensor to which the sensor device is used, each electrode 11A through 14A is connected into the same sample. However, the respective components different for each electrode from one sample can once be detected and estimated. In the case of the structure shown in FIGS. 1a and 1b, four components from one sample can once be detected and estimated.

In addition, since it becomes unnecessary to operate the probe in the QCM sensor of the conventional multi-channel type, the stable measurement can be made without change in a measurement condition. Furthermore, it is resulted in such a simple arrangement that the sensor device is merely connected to one or each measurement device.

(Second Embodiment)

It is unnecessary to separate an interval between each electrode sufficiently since in the sensor device of the multi-channel structure shown in FIGS. 1a and 1b, it is sufficiently predicted that an oscillation energy coupling between each adjacent electrode occurs.

A detailed analysis on an energy containment condition due to the electrodes formed on the crystal oscillator has been made by William Shokley et al.

Figure 2:
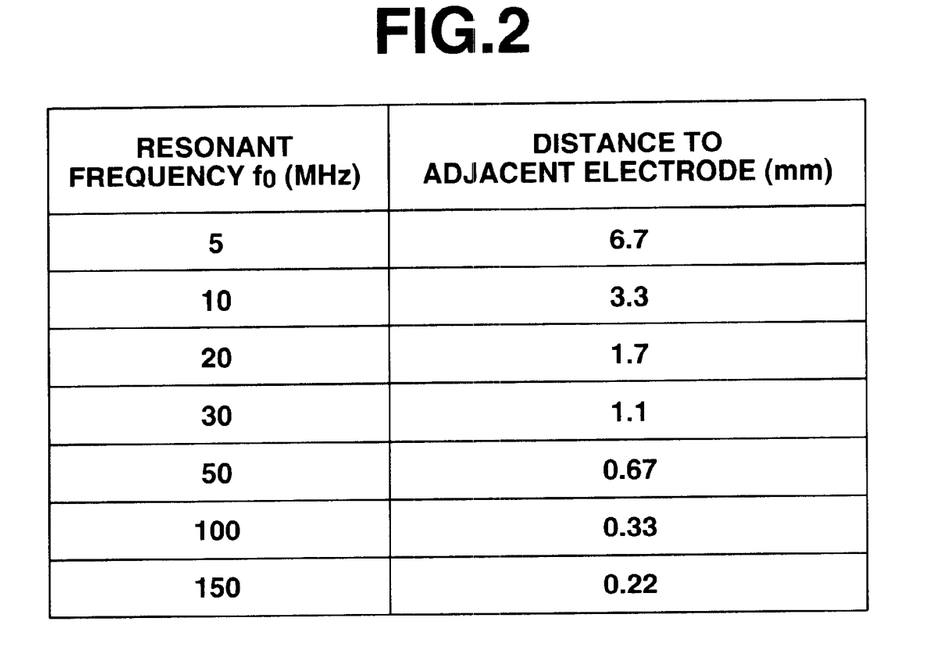
FIG. 2 is a table representing a distance by which a sufficient attenuation of a mechanical oscillation is obtainable with respect to a resonant frequency fo relating to a ratio L/t between a distance L from an end of one electrode to an end of the other electrode which is adjacent to the one electrode and a thickness t of the crystal.

In the second embodiment, an electrode film thickness is taken to have a sufficient thickness in order to prevent a mutual interference between the adjacent electrodes from occurring and the distance to an adjacent electrode with the fundamental oscillation sufficiently contained on the electrodes is restricted equal to or higher than the value recited in a table of FIG. 2.

It is noted that, in FIG. 2, a ratio of L/t on a distance L from an end of the electrodes to an end of the adjacent electrodes with respect to the crystal thickness t is concerned, the distance such that a sufficient attenuation on a mechanical oscillation is obtained is prescribed.

In the second embodiment, the above-described ratio L/t is equal to or higher than 20 in the case of each circular electrode.

According to the QCM sensor using the sensor device under this condition, a highly accurate measurement without the mutual interference between the adjacent electrodes can be achieved and the dimension of the whole sensor device can be minimized.

(Third Embodiment)

As described above, it is necessary to provide the sufficient inter-electrode distance between the respective electrodes in order to eliminate the mutual interference in the case of the multi-channel QCM sensor device shown in the first embodiment. Hence, the whole dimension of the sensor device becomes large. Then, although the dimension is minimized, the restriction of the dimension is made within the range described in the second embodiment.

Figure 3:
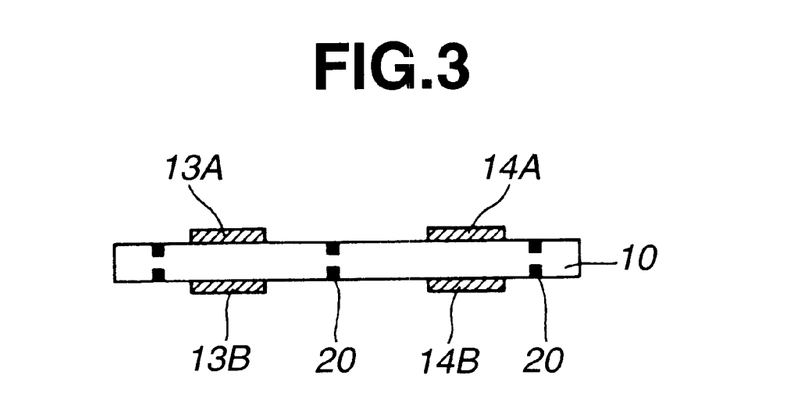
FIG. 3 is a side view of a sensor device in a third preferred embodiment according to the present invention.

FIG. 3 shows a side view of the sensor device in a third preferred embodiment according to the present invention.

In the third embodiment, each separation groove 20 is disposed between each of the electrodes and a corresponding adjacent electrode to contain the oscillation energy. Consequently, a leakage of the mechanical oscillation between each channel can be reduced.

Figure 4:
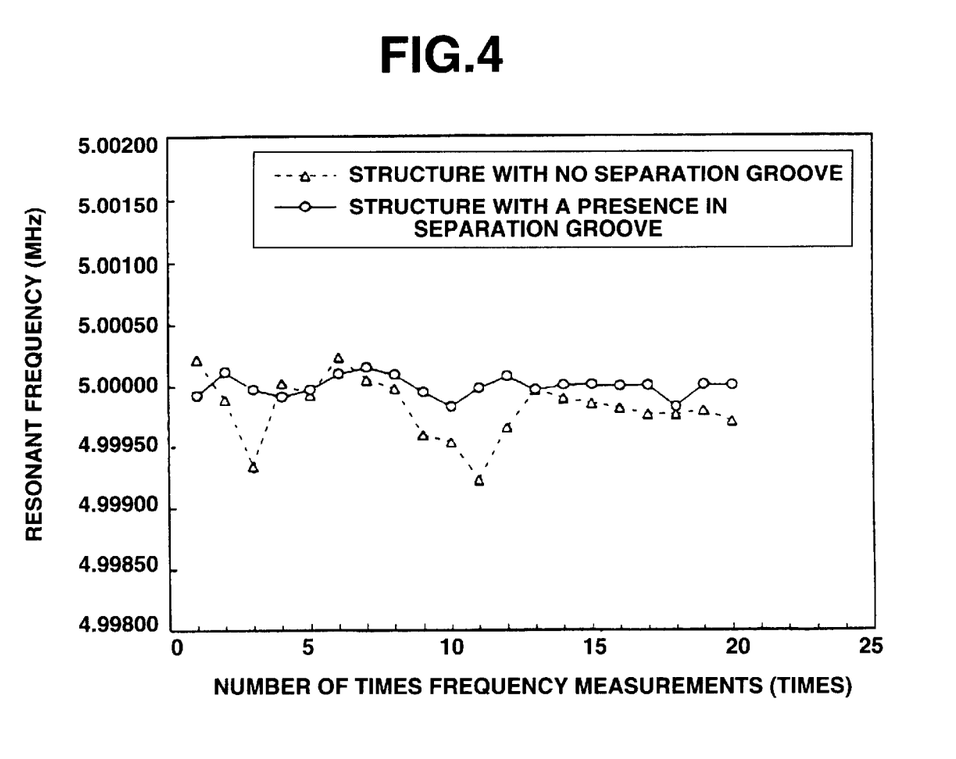
FIG. 4 is a characteristic graph of a measured frequency deviation in a case where a separation groove is installed.

The disposition of each separation groove 20 could achieve a stabilization of the measured frequency. FIG. 4 shows measurement deviations due to repetitions of the measured frequencies for the sensor device with no separation groove and for that with the separation grooves 20. It was appreciated that the deviations become reduced in the case of the sensor device with the separation grooves.

Hence, since each separation groove 20 serves to attenuate forcefully the mechanical oscillation, it becomes possible to shorten the inter-electrode distance as compared with the sensor device in the first or second embodiment. The small sizing of the sensor device can be achieved.

Furthermore, in a case where the QCM sensor is used in the solution system, a method of making an anti-water treatment using an O ring as shown in FIG. 17 is carried out for the crystal substrate. There is a possibility that the crystal substrate is distorted so that the oscillation frequency is shifted (toward a higher frequency) due to a force of the O ring pressing the crystal substrate of the sensor device with no separation groove. However, in the third embodiment, it was indicated that each separation groove could effectively be acted upon such a phenomenon as described above so that no shift in the frequency occurred.

It is noted that although the third embodiment can be applied to the multi-channel structure in the first embodiment, the reduction of the mutual interference can be assured by the structure in the third embodiment in combination with the condition described in the second embodiment.

(Fourth Embodiment)

In each of the first and third embodiments, the sensor device has the fundamental oscillation frequency of approximately 5 MHz.

This is because, in a case where, as described in the third embodiment, a shield is carried out to separate the sample atmosphere from the measurement circuit portion. In this case, a substrate thickness of at least 0.25 mm or thicker is required to reduce the crack and strain (distortion) of the crystal substrate.

On the other hand, as described in the BACKGROUND OF THE INVENTION, it is necessary to use a high frequency oscillator having a thin thickness in order to obtain a high sensitivity sensor.

Figure 5:
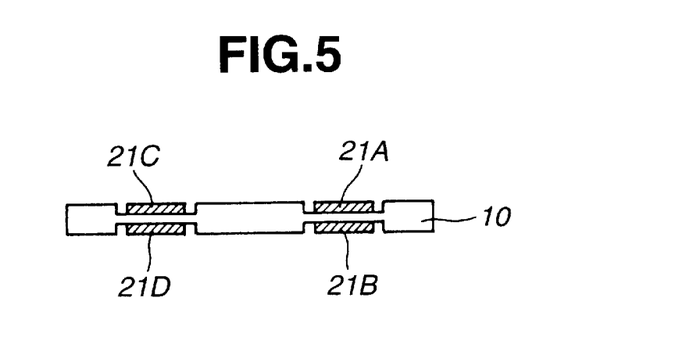
FIG. 5 is a side view of a sensor device in a fourth preferred embodiment according to the present invention.

In a fourth embodiment, as the sensor suitable for the multi-channel purpose, a surrounding portion of the crystal substrate 10 is made thick to secure a mechanical strength and portions of the oscillator in which the electrodes 21A, 21B, 21C, and 21D are formed are made thin, in order to be enabled for the high frequency application, as shown in FIG. 5.

For example, each electrode film formed portion of the substrate in an one-inch square is etched up to a thickness such that the fundamental resonant frequency is equal to or below 10 MHz.

The inter-electrode distance, in this example, is more shortened to make a miniaturization of the sensor device since the thickness of the electrode portion is made thin and the mutual interference between the electrodes can more be reduced.

The QCM sensor device based on the fourth embodiment has been produced as a prototype having the frequency of the oscillator portion ranging from 10 to 150 MHz.

The distance between the electrodes is shortened to a value equal to that shown in the second embodiment or to a value further shorter than that shown in the second embodiment.

For example, no mutual frequency interference was observed from the sensor device of 10 MHz oscillation frequency even if the ratio L/t of the distance L from the end of the one electrode to the end of the adjacent electrode is set to 16 or less.

In order to verify that the sensor device in this embodiment can be used to measure the frequency variation and serial resonance resistance without the mutual interference between the channels, an experiment was carried out.

Figure 6:
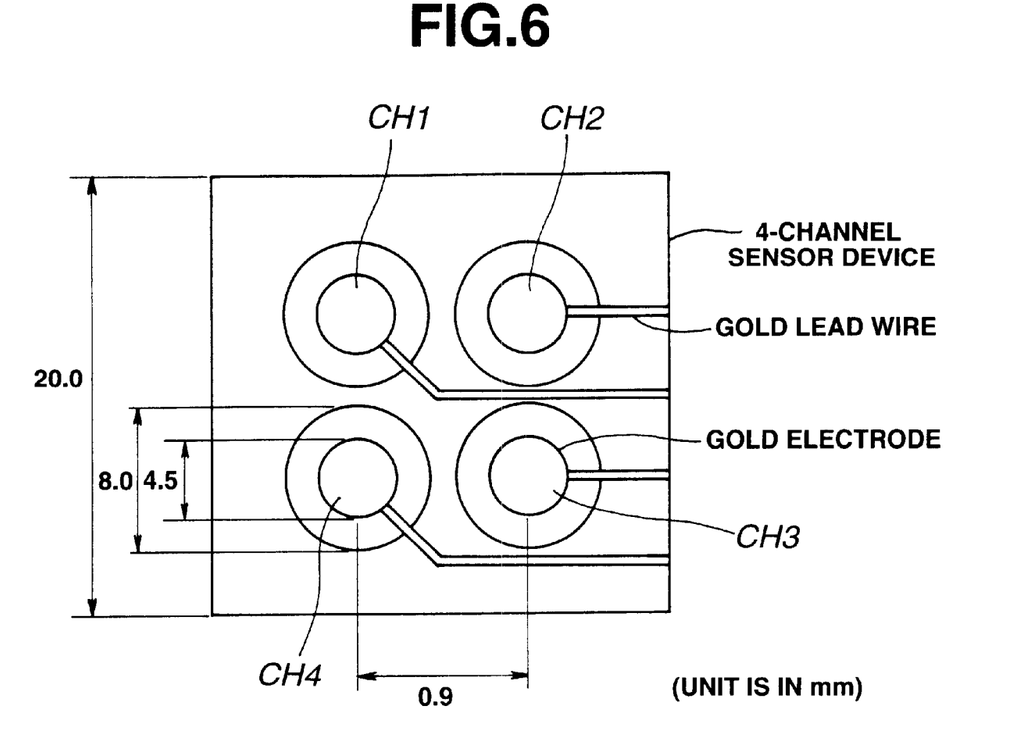
FIG. 6 is a plan view of the sensor device used in an experiment on a mutual interference between the electrodes.

The sensor device used for this experiment was formed with four-channel CH1 through CH4, as shown in FIG. 6.

This sensor device had the crystal substrate of two sheets of gold electrodes nipped. The substrate size had 200 mm square and its thickness was 267 μm. A surrounding portion around each gold electrode on the corresponding front or rear surface was engraved to have a diameter of 8.0 mm and a depth of 50 μm by means of a wet etching. Each thickness of the respective electrode portions was 167 μm and had the fundamental resonance frequency fo of 10 MHz.

For each gold electrode, chronium was laid on the crystal substrate to adhere the crystal substrate to gold and gold of 1000 Angstrom and of a diameter of 4.5 mm was evaporated and a width of each gold lead wire was 0.5 mm.

Figure 7:
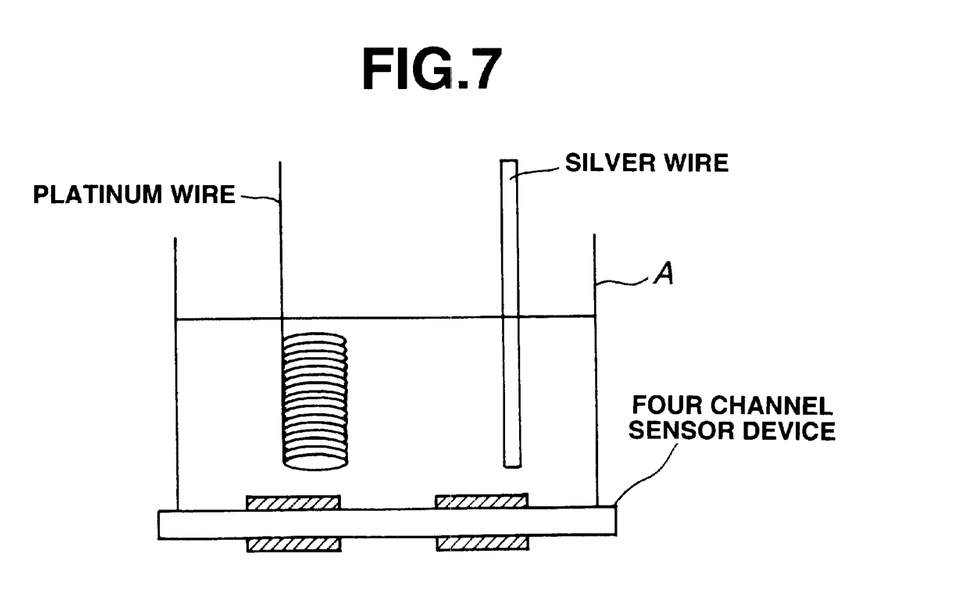
FIG. 7 is a device for depositing silver used in the experiment on the mutual interference between the electrodes.

This type of the sensor device constituted a multi-channel crystal oscillation electrolyte cell having a working electrode as the sensor device, an opposing electrode of a platinum wire, and a reference electrode of a silver wire, the sensor device thereof being attached onto a bottom portion of a vessel A and immersing a silver nitrate ($AgNO_3$) of $1\times10^{-3}$ and including a perchloric acid ($HclO_4$) of 0.2 mol as a sustaining salt within the vessel.

Figure 8:
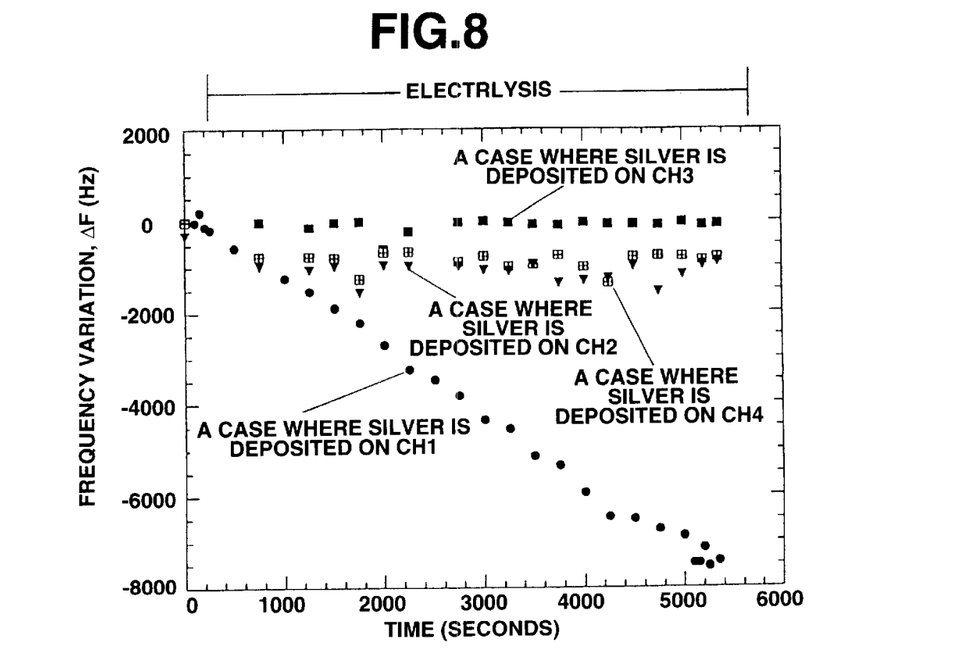
FIG. 8 is a characteristic representing a frequency variation $\Delta F$ for each channel in the experiment on the mutual interference between the electrodes.

A constant current electrolyte of 1 μA was carried out separately for each electrode of the sensor device using the electrolyte cell. Then, silver wad deposited. The frequency variation ΔF (Hz) of the channel CH1 and the serial resonance resistor $R_1$ (Ω) when silver is deposited on each electrode were measured. The experiment indicated that the frequency variation ΔF (Hz) was greatly developed when silver was deposited on the channel CH1 and was extremely small on each of the other channels CH2 through CH4, as shown in FIG. 8.

Figure 9:
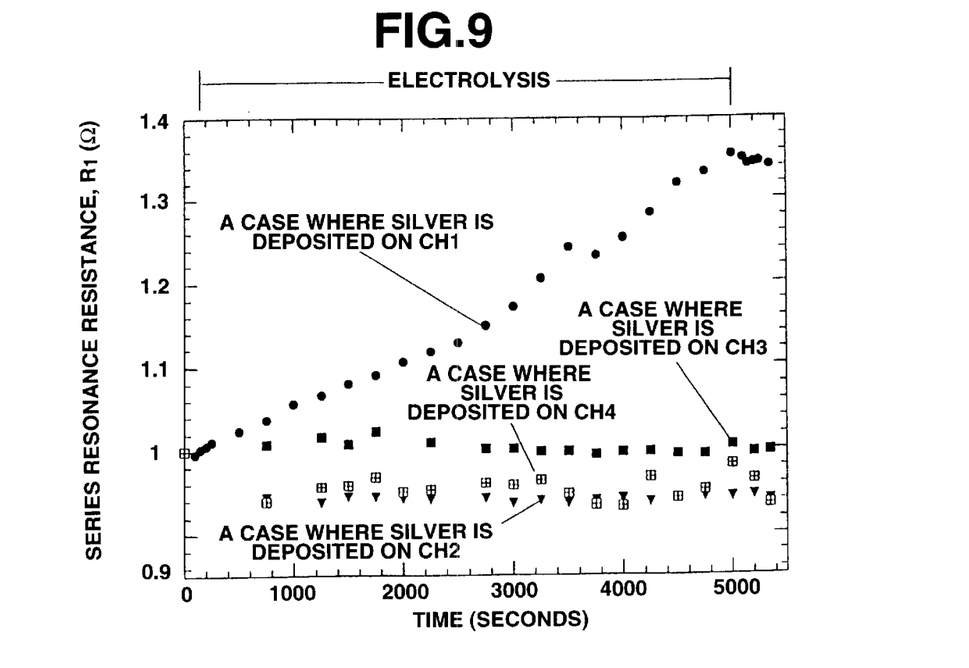
FIG. 9 is a characteristic graph representing a serial resonant resistance for each channel in the experiment on the mutual interference between the electrodes.

The serial resonance resistance variation was shown in FIG. 9. In this case, the variation in the resistance $R_1$ was large when silver was deposited on the channel CH1. However, in a case where silver was deposited on the other channels CH2 through CH4, the resistance variation was extremely small.

From these facts, the respective channels of the four-channel sensor device were independent mutually from each other and it was appreciated that the detection and estimation measurement could be made for each channel without occurrence of the mutual interference.

As another experiment to verify that the mutual interference between the respective channels can be eliminated, the frequency variation ΔF and serial resonance resistance $R_1$ on the channel CH1 were measured when the water drop of 70 μl (microliter) was individually laid on each channel of the four-channel sensor device shown in FIG. 6.

Figure 10:
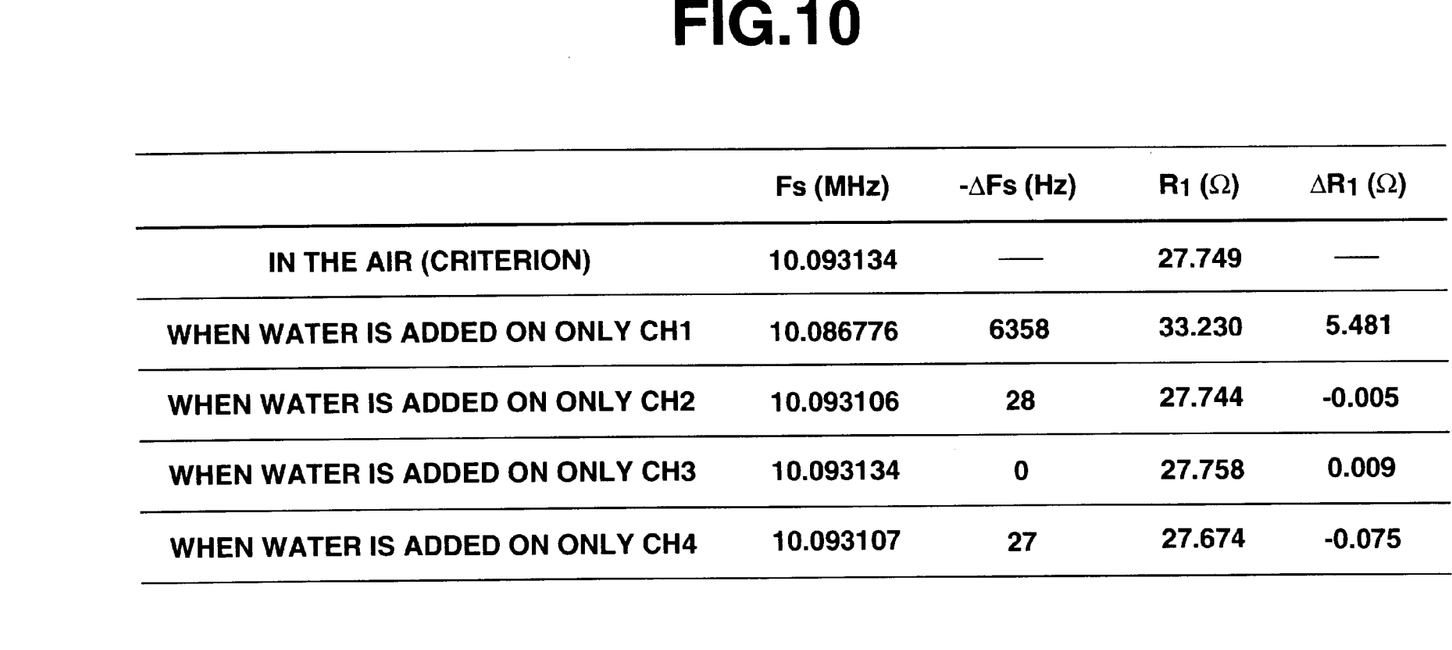
FIG. 10 is a table representing variations in the frequency and serial resonant resistor when a water drop is laid on each channel in the experiment on the mutual interference between the electrodes.

This consequence was obtained as shown in table of FIG. 10.

As appreciated from this table, the frequency variation and resonance resistance variation were remarkable in a case where the water drop was laid only on the channel CH1.

In a case where the water drop was laid on one of the other channels CH2 through CH4, the frequency variation of the channel CH1 was 1% or less and the variation of the resistance was 2% or less so that almost no variation in the frequency variation and in the resistance occurred.

This result indicated that each channel was respectively independent and the detection and estimation measurement could be made without occurrence of the mutual interference.

It is noted that although the sensor device in the fourth embodiment is applicable to the multi-channel structure of the first embodiment, the combination of each separation groove in the third embodiment can be achieved.

(Fifth Embodiment)

In the QCM sensor device in a fifth embodiment, the etching process of the crystal substrate of approximately 6 MHz is made thin for the high frequency application purpose.

However, if the frequency becomes higher than 50 MHz, the quantity of etching is reached to 244 μm.

Hence, at the same time when it takes long to perform the etching, a frequency error between the respective channels and between the individual sensor devices is predicted to occur.

Figure 11:
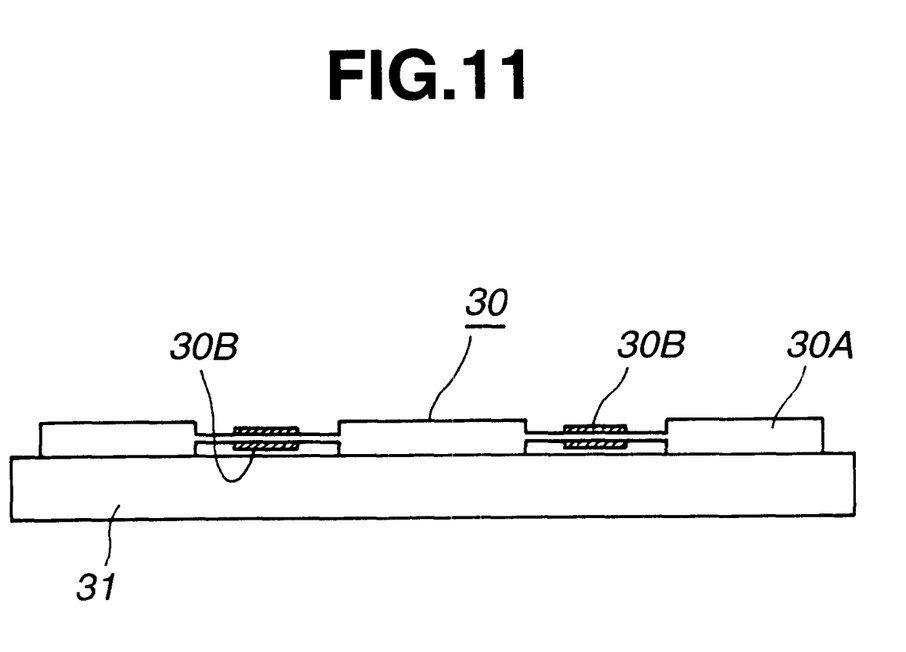
FIG. 11 is a side view of a sensor device in a fifth preferred embodiment according to the present invention.

In this embodiment, as shown in FIG. 11, in the thin crystal substrate 30A for the high frequency purpose having the thickness of approximately 80 μm was etched and the electrode 30B was formed on a part engraved to a predetermined thickness by means of a small quantity of etching. The sensor device main body 30 is adhered to the crystal substrate 31 (or quartz substrate) having approximately 250 μm to constitute the crystal substrate 31 as the substrate holder.

It is noted that a flexible material having a low elasticity is preferably used as an adhesive by which the sensor device main body 30 is adhered onto the crystal substrate in order not to develop a stress generated on the electrode portion and its surrounding portion as least as possible.

In the fifth embodiment, only an etching for the relatively thin crystal substrate can be carried out to manufacture the sensor device for the high frequency purpose, a time duration of the etching process can be shortened, and a deviation of the etching quantity can be eliminated.

It is noted that the fifth embodiment may be applied to the fourth embodiment and the sensor device main body can be the structure having the separation grooves in the third embodiment.

In each preferred embodiment, the material for each electrode is made of gold. However, a gold-chronium electrode may be used as the electrode material, the gold electrode having a chronium layer having 50 Angstrom to 500 Angstrom thickness interposed between the crystal substrate and gold electrode.

Furthermore, in place of chronium, titanium or nickel may be used.

In addition, in each embodiment, the number of the electrodes are four and the number of the channels are four.

However, recently, an artificial crystal of a diameter 100 mm has been grown up with a species crystal being grown up by means of a water hot synthetic method under a high temperature and a high pressure in a stripe-shaped autograve made of a special steel. Hence, in the QCM sensor device in each embodiment, a large-sized crystal substrate having , e.g., a diameter of 10 mm may be used with the number of electrodes having arbitrary to array a multiple number of electrodes.

Furthermore, it is not necessary to make the area of the electrodes formed on the front surface equal to that formed on the rear surface.

In each embodiment, the crystal substrate is used as the substrate. A Langasite crystal having a large mechanical coupling coefficient may be used.

Industrial Application Possibility

As described hereinabove, the QCM sensor according to the present invention is suitably used for the stable and high-frequency measurement sensor for detecting and estimating (quantitatively analyzing) the components of the sample, with the sensor device immersed into a sample gas or sample solution and achieving the multi-channel sensor device to detect and estimate the components once by one sample.

What is claimed is:

1. A QCM sensor including a sensor device, the sensor device having a crystal substrate, having a first pair of electrodes and second pair of electrodes on the front and back surfaces of the crystal substrate, respectively, the first and second pairs of electrodes being disposed so as to oppose with each other via the crystal substrate and the QCM sensor detecting and quantitatively analyzing components of a sample from either a variation in a fundamental resonant frequency or a variation in an impedance when a surface of one of the first and second pairs of electrodes is immersed into either a sample gas or a sample solution, improvements wherein the sensor device is arranged in a multi-channel configuration such that electrodes in each of the first and second pairs of electrodes are disposed on the respective front and rear surfaces of the crystal substrate so as to adjoin to one another, each electrode is arranged to enable a fixation of a receptor which is different for each component of the sample to be detected and quantitatively analyzed, and wherein each electrode of the sensor device is of an approximately circular shape and a ratio of L/t of a distance (L) between each electrode and its adjacent electrode in each of the first and second pair of electrodes to a thickness (t) of the crystal substrate is set to 20:1 or more.

2. A QCM sensor as claimed in claim 1, wherein the crystal substrate of the sensor device is discontinuous in such a manner that a first part of the substrate of a forming portion of each electrode is made thinner than a second part of the substrate of a surrounding portion of each electrode.

3. A QCM sensor as claimed in claim 1, wherein the sensor device uses a Langasite crystal in place of the crystal substrate.

4. A QCM sensor including a sensor device, the sensor device having a crystal substrate, having a first pair of electrodes and second pair of electrodes on the front and back surfaces of the crystal substrate, respectively, the first and second pairs of electrodes being disposed so as to oppose with each other via the crystal substrate and the QCM sensor detecting and quantitatively analyzing components of a sample from either a variation in a fundamental resonant frequency or a variation in an impedance when a surface of one of the first and second pairs of electrodes is immersed into either a sample gas or a sample solution, improvements wherein the sensor device is arranged in a multi-channel configuration such that electrodes in each of the first and second pairs of electrodes are disposed on the respective front and rear surfaces of the crystal substrate so as to adjoin to one another, each electrode is arranged to enable a fixation of a receptor which is different for each component of the sample to be detected and quantitatively analyzed, and wherein the crystal substrate of the sensor device is provided with a separation groove between each of the electrodes and its adjacent electrode in each of the first and second pair of electrodes, the separation groove being not fully penetrated through the crystal substrate and reducing an oscillation energy coupling between the electrode and its adjacent electrode.

5. A QCM sensor as claimed in claim 4, wherein the crystal substrate of the sensor device is discontinuous in such a manner that a first part of the substrate of a forming portion of each electrode is made thinner than a second part of the substrate of a surrounding portion of each electrode.

6. A QCM sensor as claimed in claim 4, wherein the sensor device includes a sensor device main body using a thin crystal substrate for a high frequency purpose to make a first part of the substrate of a forming portion of each electrode thinner than a second part of the substrate of its surrounding portion of each electrode and a substrate holder made of the crystal substrate or of a quartz substrate and having a thickness thicker than the sensor device main body, and onto which the sensor device main body is adhered.

7. A QCM sensor as claimed in claim 4, wherein the sensor device uses a Langasite crystal in place of the crystal substrate.

8. A QCM sensor including a sensor device, the sensor device having a crystal substrate, having a first pair of electrodes and second pair of electrodes on the front and back surfaces of the crystal substrate, respectively, the first and second pairs of electrodes being disposed so as to oppose with each other via the crystal substrate and the QCM sensor detecting and quantitatively analyzing components of a sample from either a variation in a fundamental resonant frequency or a variation in an impedance when a surface of one of the first and second pairs of electrodes is immersed into either a sample gas or a sample solution, improvements wherein the sensor device is arranged in a multi-channel configuration such that electrodes in each of the first and second pairs of electrodes are disposed on the respective front and rear surfaces of the crystal substrate so as to adjoin to one another, each electrode is arranged to enable a fixation of a receptor which is different for each component of the sample to be detected and quantitatively analyzed and wherein the crystal substrate of the sensor device is discontinuous in such a manner that a first part of the substrate of a forming portion of each electrode is made thinner than a second part of the substrate of a surrounding portion of each electrode.

9. A QCM sensor as claimed in claim 8, wherein the sensor device includes a sensor device main body using a thin crystal substrate for a high frequency purpose to make a first part of the substrate of a forming portion of each electrode thinner than a second part of the substrate of its surrounding portion of each electrode and a substrate holder made of the crystal substrate or of a quartz substrate and having a thickness thicker than the sensor device main body, and onto which the sensor device main body is adhered.

10. A QCM sensor as claimed in claim 8, wherein the sensor device uses a Langasite crystal in place of the crystal substrate.

11. A QCM sensor including a sensor device, the sensor device having a crystal substrate, having a first pair of electrodes and second pair of electrodes on the front and back surfaces of the crystal substrate, respectively, the first and second pairs of electrodes being disposed so as to oppose with each other via the crystal substrate and the QCM sensor detecting and quantitatively analyzing components of a sample from either a variation in a fundamental resonant frequency or a variation in an impedance when a surface of one of the first and second pairs of electrodes is immersed into either a sample gas or a sample solution, improvements wherein the sensor device is arranged in a multi-channel configuration such that electrodes in each of the first and second pairs of electrodes are disposed on the respective front and rear surfaces of the crystal substrate so as to adjoin to one another, each electrode is arranged to enable a fixation of a receptor which is different for each component of the sample to be detected and quantitatively analyzed, and wherein each electrode of the sensor device is of an approximately circular shape and a ratio of L/t of a distance (L) between each electrode and its adjacent electrode in each of the first and second pair of electrodes to a thickness (t) of the crystal substrate is set to 20:1 or more, and wherein the crystal substrate is provided with a separation groove between each of the electrodes and its adjacent electrode in each of the first and second pair of electrodes, the separation groove being not fully penetrated through the crystal substrate and reducing an oscillation energy coupling between the electrode and its adjacent electrode.

12. A QCM sensor as claimed in claim 11, wherein the sensor device uses a Langasite crystal in place of the crystal substrate.

13. A QCM sensor as claimed in claim 11, wherein the crystal substrate of the sensor device is discontinuous in such a manner that a first part of the substrate of a forming portion of each electrode is made thinner than a second part of the substrate of a surrounding portion of each electrode.

14. A QCM sensor as claimed in claim 13, wherein the sensor device uses a Langasite crystal in place of the crystal substrate.

15. A QCM sensor as claimed in claim 11, wherein the sensor device includes a sensor device main body using a thin crystal substrate for a high frequency purpose to make a first part of the substrate of a forming portion of each electrode thinner than a second part of the substrate of its surrounding portion of each electrode and a substrate holder made of the crystal substrate or of a quartz substrate and having a thickness thicker than the sensor device main body, and onto which the sensor device main body is adhered.

16. A QCM sensor as claimed in claim 15, wherein the sensor device uses a Langasite crystal in place of the crystal substrate.

* * * * *